United States Patent
Flick, III (10) Patent No.: US 12,029,886 B2
(45) Date of Patent: Jul. 9, 2024

(54) THERMOFORMED MEDICAL SYRINGE

(71) Applicant: Conrad A. Flick, III, Bettendorf, IA (US)

(72) Inventor: Conrad A. Flick, III, Bettendorf, IA (US)

( * ) Notice: Subject to any disclaimer, the term of this patent is extended or adjusted under 35 U.S.C. 154(b) by 173 days.

(21) Appl. No.: 17/228,867

(22) Filed: Apr. 13, 2021

(65) Prior Publication Data

US 2022/0323688 A1    Oct. 13, 2022

(51) Int. Cl.
*A61M 5/32* (2006.01)
*A61M 5/31* (2006.01)

(52) U.S. Cl.
CPC ........ *A61M 5/3202* (2013.01); *A61M 5/3137* (2013.01)

(58) Field of Classification Search
CPC ..... A61M 5/3202; A61M 5/3137; A61M 5/32
See application file for complete search history.

(56) References Cited

U.S. PATENT DOCUMENTS

| | | | |
|---|---|---|---|
| 2,725,057 A | 11/1955 | Lockhart | |
| 4,772,267 A | 9/1988 | Brown | |
| 5,037,393 A | 8/1991 | Ellgass | |
| 5,746,733 A * | 5/1998 | Capaccio | A61M 5/3202 604/240 |
| 9,259,538 B2 | 2/2016 | Caizza et al. | |
| 9,458,536 B2 * | 10/2016 | Felts | A61B 5/150236 |
| 10,071,208 B2 | 9/2018 | Marti | |
| 10,857,306 B2 | 12/2020 | Holmqvist et al. | |
| 10,918,806 B2 | 2/2021 | Lu | |
| 2003/0097096 A1 | 5/2003 | Niedospial | |
| 2009/0198194 A1 | 8/2009 | Madin et al. | |
| 2010/0049141 A1 * | 2/2010 | Gardner | A61M 5/3216 604/192 |
| 2015/0165133 A1 * | 6/2015 | Zhang | A61M 5/3202 604/192 |
| 2016/0151584 A1 * | 6/2016 | Deleuil | A61M 5/344 604/263 |
| 2017/0157386 A1 | 6/2017 | Ferlic | |
| 2019/0159968 A1 | 5/2019 | Nakatsuji et al. | |
| 2020/0282130 A1 | 9/2020 | Hemminger et al. | |
| 2020/0297919 A1 | 9/2020 | Hemminger et al. | |
| 2021/0038803 A1 | 2/2021 | Chen et al. | |
| 2022/0040416 A1 * | 2/2022 | Vogt | A61M 5/344 |

\* cited by examiner

*Primary Examiner* — Brandy S Lee
*Assistant Examiner* — Fatimata Sahra Diop
(74) *Attorney, Agent, or Firm* — Foley & Lardner LLP (57) ABSTRACT

A syringe with a tube having an open proximal end and a sealed, truncated, distal end fluidly communicating via a stepped lumen. The syringe has a distal intravenous cannula; and a shaft supporting a distal, fluid sealing disc and a finger pad at opposite ends moveably disposed within said tube. The syringe features a syringe body which is economically thermoformed from an extruded tube.

5 Claims, 8 Drawing Sheets

THERMOFORMED MEDICAL SYRINGE

BACKGROUND OF THE INVENTION

Field of the Invention

The present invention relates to a medical syringe device for safely and facilely administering a fluid injectant into a patient. More particularly, the invention relates to the economical manufacture of efficient, single-use syringes for injecting fluids or gels into patients with improved sustainability. The syringe device's barrel and plunger can be economically thermoformed and die cut using extruded tubing and flat sheet material, respectively. The syringe appearance will be similar to a common syringe and easily adaptable to current administering techniques.

The use of conventional syringes for patient injections is known. A syringe device typically comprises: a rigid, circular, cylindrical barrel defining a fluid volume retaining chamber with an open, flanged proximal end and a closed, distal wall having a central frustum with a fluid passageway communicating the barrel with an attached distally extending cannula. A plunger extends proximally from the barrel supporting a distal grommet in a fluid-tight engagement with the barrel. A needle protective cap is frictionally positioned distally on the barrel for transporting and disposal; and/or a rotating sheath can be attached distally for safe disposal. The components are typically injection molded separately, assembled, packaged, and sterilized.

One embodiment of this invention relates to a syringe body which is thermoformed using extruded tubing. The body's barrel is thermoformed with an open, flanged, proximal end and a sealed, distal end with a fluid passageway in the selvage communicating with a distally attached needle. The plunger is also thermoformed from die cut flat sheet creating a rigid shaft with a distal, integral, fluid sealing disc and a proximal, integral, finger pad disc. The needle sheath is a proximally flanged, distally sealed, and intermittently die-cut extruded tube. It slidably attaches by engaging the sealing selvage of the body.

Another embodiment thermoforms the needle, trough sheath integral with the barrel's sealing flange via a living hinge with needle rotational interference, or thermally attached with a biased hinge, both for selective, sheath positioning.

This design and manufacturing provides the syringe with cost economies by several reductions: component numbers, material thickness formerly required for injection molding, speed of manufacturing, and sustainability. The packaging requirements are simplified by its narrow profile, similar to a paper sleeve for a soda straw.

The difficulties and limitations suggested in the preceding and desired features are not intended to be exhaustive but rather are among many which may tend to reduce the effectiveness and user satisfaction with previously known syringes. Other noteworthy problems and limitations may also exist; however, those presented above should be sufficient to demonstrate that syringes appearing in the past will admit to worthwhile improvement.

BRIEF SUMMARY

One preferred embodiment of the invention which is intended to address concerns and accomplish at least some of the foregoing objects comprises a syringe body thermoformed from an extruded tube. Extruded tubing permits a barrel sidewall to have a uniform thickness and a consistent interior diameter with no molding draft to affect the plunger sealing engagement. The syringe body has a thermoformed flange about its proximal opening and a sealed, truncated distal end with a fluid passageway communicating with a distal needle. The truncated distal end is achieved with axial pressure applied to barrel during the sealing process. This configuration combined with material thickness establish the needles posture. The needle is attached within this passageway with an applied adhesive. This embodiment resembles a typical syringe in appearance and functionality. This barrel and plunger are sufficiently rigid for gripping when drawing a medicament dosage and administering an injection. The material selection will be based on biocompatibility and sustainability.

The plunger is die cut from flat stock and consists of a shaft with stiffening, folded sidewalls supporting integral, thermally rotated discs. As the sealing disc is thermally rotated, its attachment/pivot points to the shaft are blended into the diameter of the circular sealing disc establishing a uniform, circular seal.

In another embodiment, the syringe body barrel, with integral sheath, is thermoformed from a similar section of extruded tubing. The proximal, open end is thermally flanged for rigidity and providing a gripping means. At an intermediate distance from the proximal end, the tube is thermoformed and sealed over a mandrel to create a cylindrical barrel with a truncated distal end having a stepped frustum shaped, central opening to receive a distal cannula with adhesive. The barrel's frustum increases the distal wall rigidity for the needle. A small opening, perhaps a simple slit, is die cut at the frustum distal termination creating the needle seat. The distal remainder of the sealed tubing beyond the seal is thermoformed slightly downward permitting cannula clearance into a cannula protective trough. At its juncture with the sealed end of the barrel, a biased linear hinge is formed into the selvage to provide selective positioning of the sheath. The base of the rotating sheath interferes with the needle when rotated to establish an open or closed sheath posture. Along the sheath's sidewall length, two detents are formed in the sidewalls with a sufficient depth to engage the cannula when the trough is formed providing selective sheath closure.

The plunger is preferably an injection molded piece with a central, half cylindrical shaft supporting an integral finger pad and an opposing sealing disc. The mold detail for the sealing disc is an undercut to provide a circular cross-section without a parting line affecting the sealing engagement with the barrel. When ejected, the sealing component slightly compresses overcoming the undercut and tumbles from the mold.

This embodiment also features an optional, outer sheath for shipping and handling. Once removed, it is discarded for the rotating sheath is implemented for disposal. The outer sheath has a flanged, open proximal end, a sealed, truncated distal end for disposal sheath clearance, and intermittent, attachment die-cuts.

In another embodiment, the barrel and integral sheath are thermoformed to accept a luer-hubbed needle. The barrel's proximal, open end is thermally flanged for rigidity and providing a gripping means. At an intermediate distance from the proximal end, the tube is die-cut, thermoformed, and sealed over a mandrel to create a barrel with a slightly, paraboloidal distal end having a central opening with a stepped frustum to receive the cannula with adhesive. This paraboloid may be circular or elliptical. The barrel's distal dome shape creates a nonlinear seal which establishes a rigid needle posture in relation to the barrel. The distal remainder of the sealed tubing is die cut and thermally formed producing a trough sheath with an open, angular projection at its base to retain the luer hub. At its juncture with the sealed end of the barrel, a biased living hinge is formed into the selvage to provide selective positioning of the sheath. Along the sheath's sidewall length, two detents are formed in the sidewalls with a sufficient depth to engage the cannula when the trough is formed providing selective sheath closure.

The plunger is die-cut with a folded configuration supporting a sealing grommet with an end geometry matching the curvatures of the barrel distal end.

The component configurations of the various embodiments may be interchanged and have a circular, elliptical, or an irregular cross-section depending on the usage and plunger sealing means.

On the body, there are graduated indicia to determine the volume within the fluid compartment in relation to the plunger's seal position within the syringe's body.

The difficulties and limitations suggested in the preceding and desired features are not intended to be exhaustive but rather are among many which may tend to reduce the effectiveness and user satisfaction with previous known syringes. Other noteworthy problems and limitations may also exist; however, those presented above should be sufficient to demonstrate that syringes appearing in the past will admit to worthwhile improvement.

DRAWINGS

Other objects and advantages of the present invention will become apparent from the following detailed description of the preferred embodiments thereof taken in conjunction with the accompanying drawings wherein.

DETAILED DESCRIPTION

Figure 1:
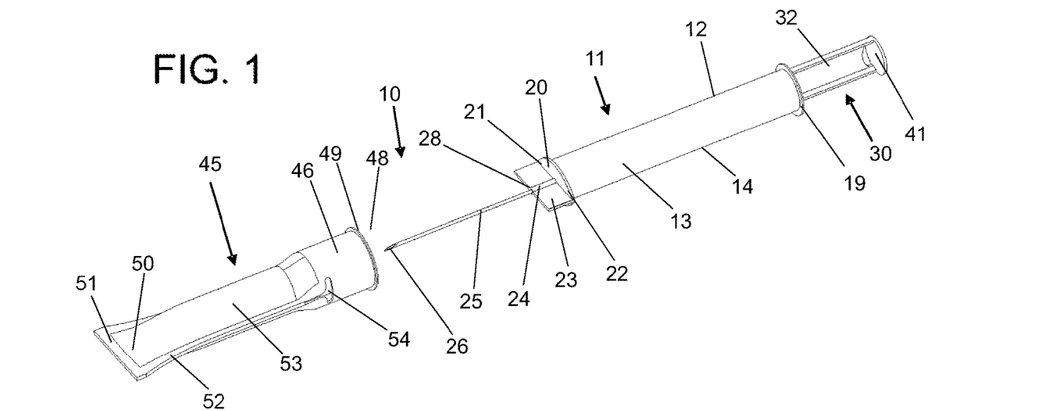
FIG. 1 is an axonometric view of a syringe body in accordance with one embodiment of the invention.
Figure 2:
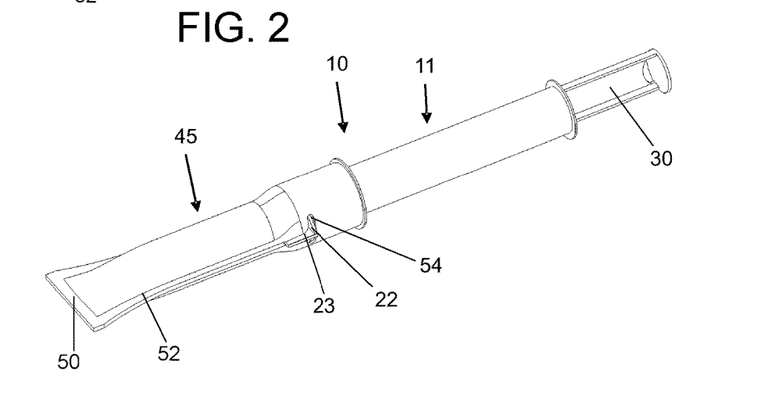
FIG. 2 is an axonometric view of the thermoformed syringe of FIG. 1 with a sheath in place.
Figure 3:
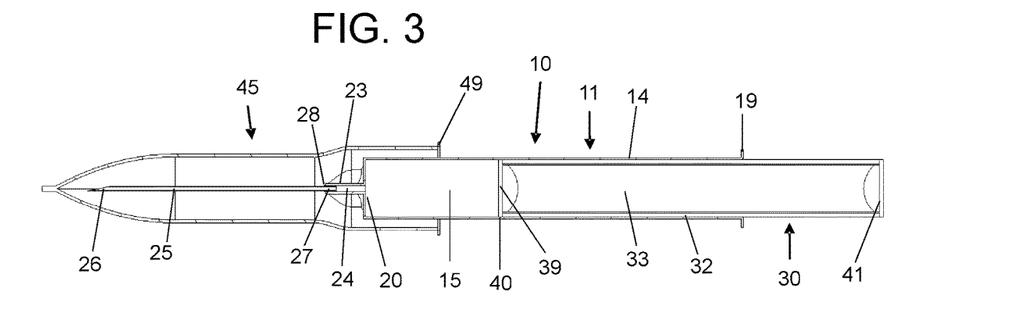
FIG. 3 is a longitudinal cross-sectional, side view of the thermoformed syringe of FIG. 1.
Figure 4:
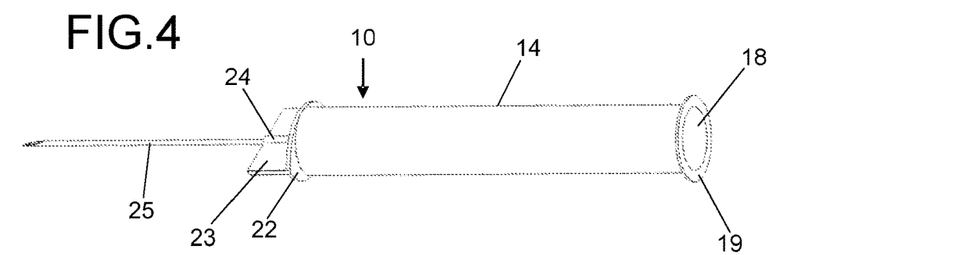
FIG. 4 is an axonometric view of a thermoformed syringe in accordance with one embodiment of the invention.
Figure 5:
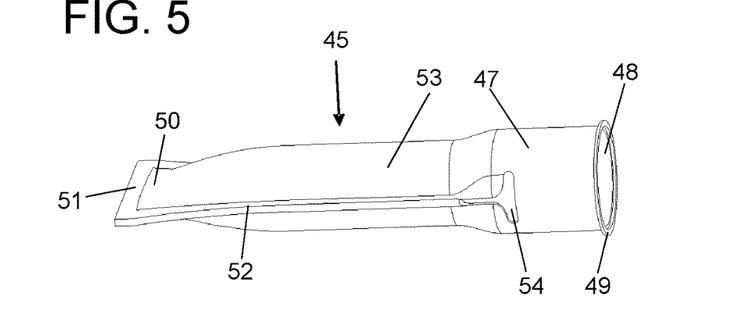
FIG. 5 is a side, axonometric view of a thermoformed sheath.
Figure 6:
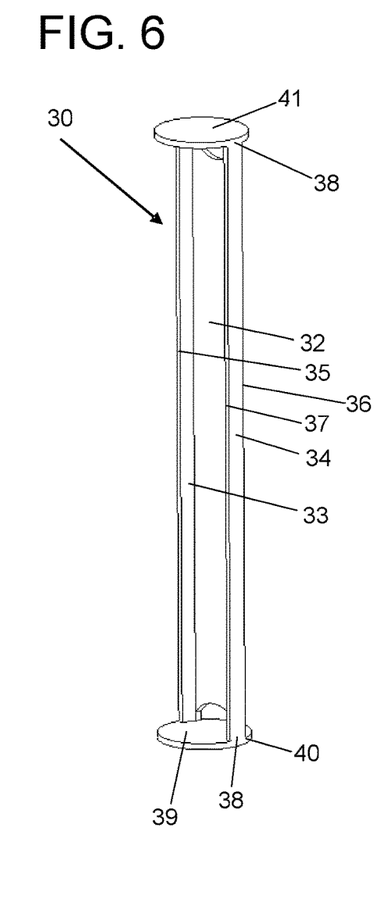
FIG. 6 is an axonometric view of a syringe's plunger.
Figure 7:
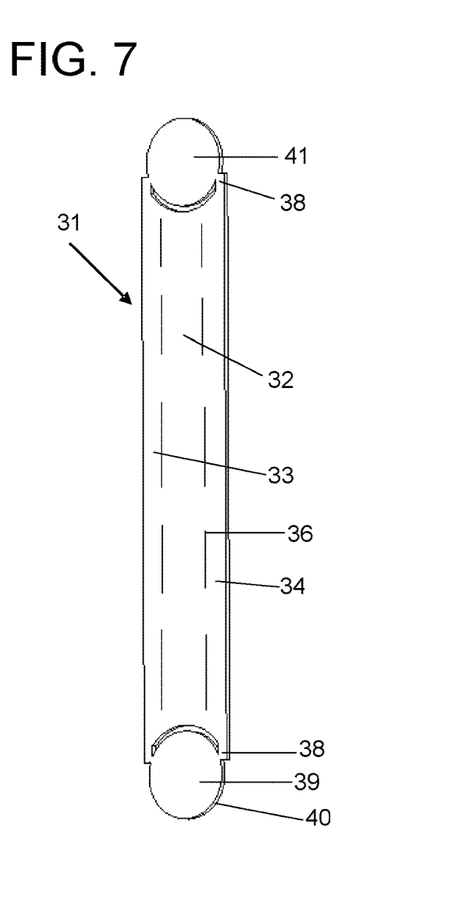
FIG. 7 is a side view of the syringe plunger die-cut blank.

Referring now particularly to the drawings, wherein like reference characters refer to like parts, and initially to FIGS. 1, 3, and 4, there will be seen an axonometric view of a thermoformed syringe 10 in accordance with one preferred embodiment of the invention. The syringe 10 in FIGS. 1, 3, and 4 comprises a tubular body 11 having a flanged, proximal opening 18 and a truncated, thermally sealed distal end 20 with a fluid passageway 24 through the sealing flange 23 fluidly communicating with an axially aligned cannula 25 (needle); and an axially sliding plunger 30 with a barrel 14 sealing means to define a fluid chamber 15. The cannula 25 has one end 26 sufficiently sharp to pierce the patient's skin and the other end 27 blunt to receive the affixing adhesive 28. The proximal flange 19 is thermoformed encircling the proximal opening 18 of barrel 14 to maintain the circular nature of the barrel 14 and assist the holding of the syringe 10 during filling and administering an injection. The barrel 14 is thermoformed and distally sealed under slight, axial pressure over a mandrel using extruded tubing 12 to establish a uniform diameter 13 throughout its entire chamber 15 length and a smooth, truncated end wall 20. As a result of the end wall 20 compression when sealing, two elliptical selvages 22 are formed flanking the distal end wall 20. They become the positioning posts for the cannula's sheath 45. Now referring to FIGS. 6 and 7, the plunger 30 is from die cut flat stock material 31 and consists of a shaft 32 with stiffening, folded sidewalls 33 and 34 supporting thermally rotated, integral seal disc 39 and finger pad disc 41. Sidewall 33 traverses the barrel diameter to guide the plunger's travels with edge 35 and fold 36 within barrel 14, and sidewall 34 stiffens and assists axial travel with contacting edge 37. As the sealing disc 39 is thermally rotated, its attachment/pivot points 38 to the shaft are thermally blended into the diameter of the circular sealing disc 39 establishing a uniform, circular liquid-tight seal 40. FIGS. 2 and 5 reveal the needle sheath 45 is a section of extruded tubing 46 with a diameter 47 sufficient to pass over the syringe body's 11 seal selvage 22. A thermal seal 50 closes the distal end 51 and partially wraps the sides 52 and has an open, flanged, proximal end 48. The proximal flange 49, like the barrel flange 19, maintains the circular nature and adds to the cylindrical rigidity of the sheath 45. The distal, partial, sidewall seal 52 reduces the sheath barrel's diameter 47 in region 53 to restrict its axial travel onto the syringe 10 protecting the cannula tip 26. Toward the proximal end 48 are two, opposing die-cut, T-shaped openings 54 to engage the flanged, selvage section 22 and flange 23 of the syringe barrel's distal seal 21 for securing the sheath's 45 position. To assemble, the sheath 45 is slightly compressed about the side-openings 54 to clear the body's sealing, selvage flange 22 as it's axially slid onto the syringe body 11 and then released to engage the selvage flange 23 for attachment. To remove, simply reverse the procedure.

Figure 8:
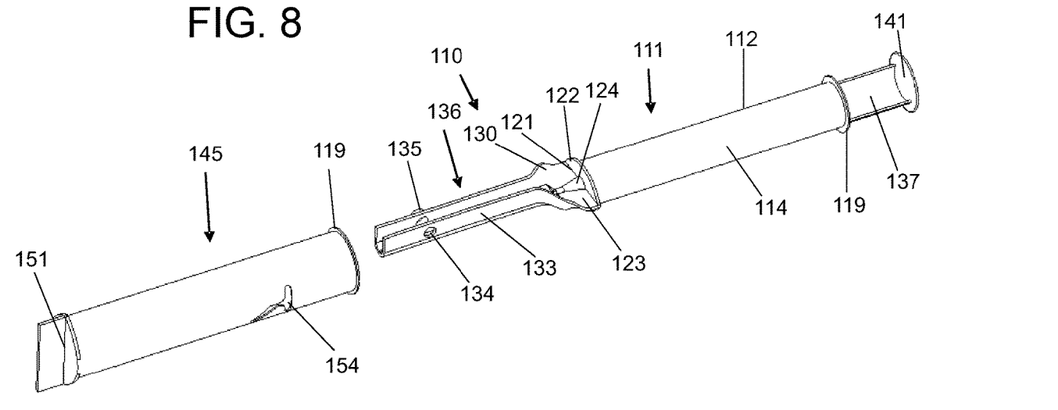
FIG. 8 is an axonometric view of a syringe in accordance with an alternative embodiment of the invention.
Figure 9:
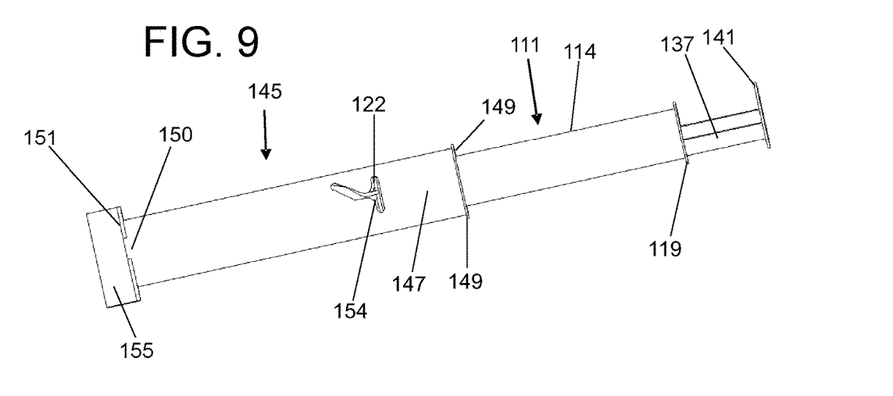
FIG. 9 is an axonometric view of the thermoformed syringe of FIG. 8 with a sheath in place.
Figure 10:
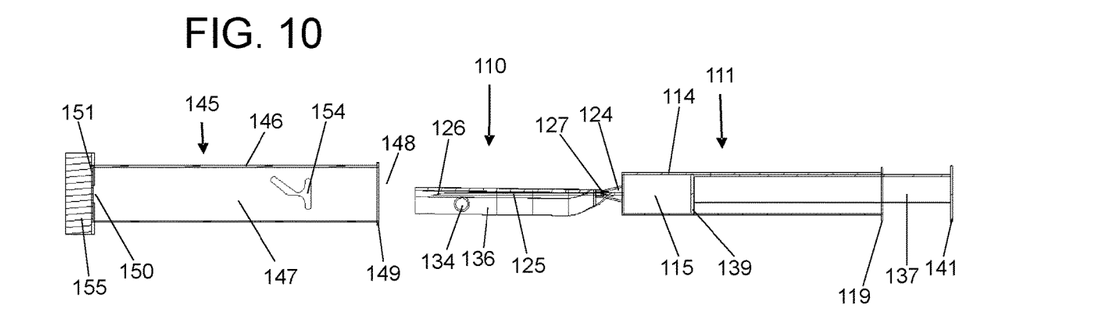
FIG. 10 is an expanded, longitudinal cross-sectional, side view of the thermoformed syringe of FIG. 8.
Figure 11:
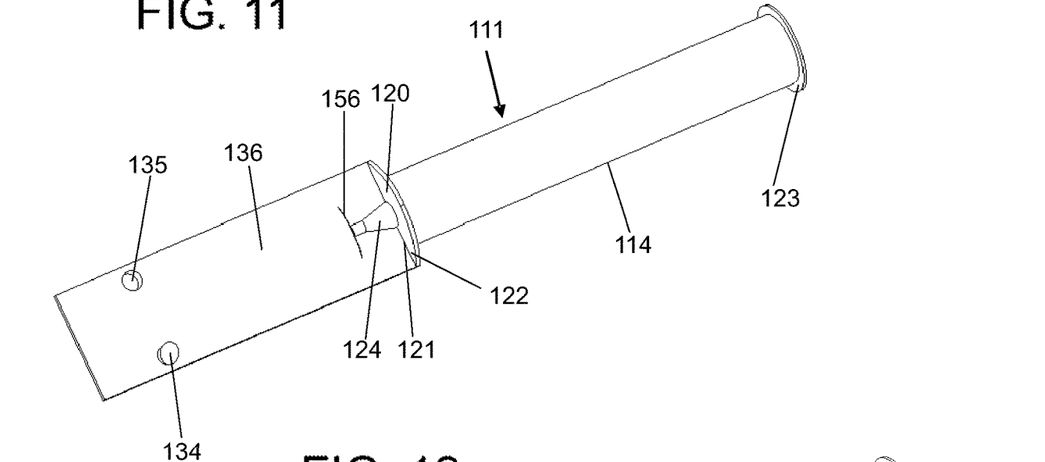
FIG. 11 is a plan, axonometric view of a thermoformed syringe showing the die-cut sheath prior to thermoforming.
Figure 12:
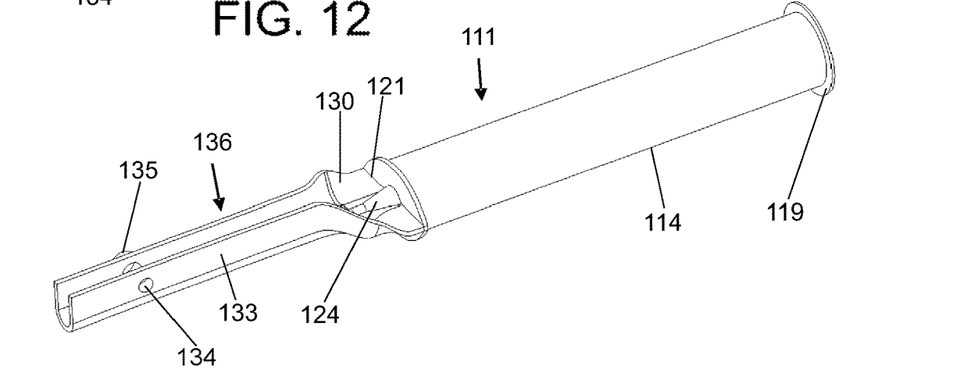
FIG. 12 is an axonometric view of a syringe with sheath in a needle protective posture.
Figure 13:
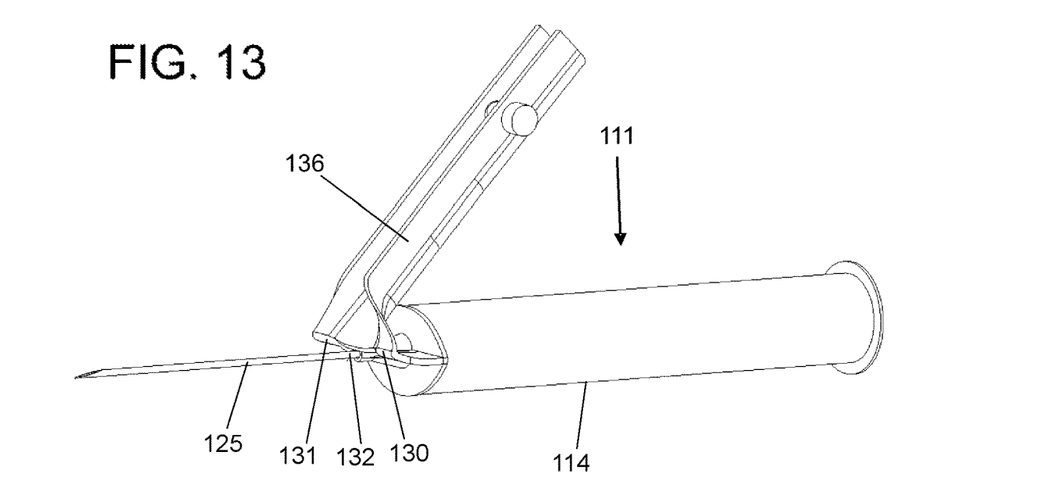
FIG. 13 is an axonometric view of a syringe with sheath in a retracted posture.
Figure 14:
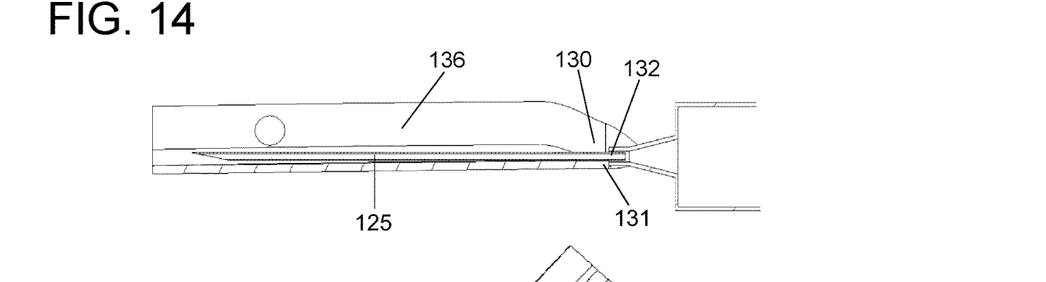
FIG. 14 is a side, cross-sectional view of a syringe with sheath in a needle protective posture.
Figure 15:
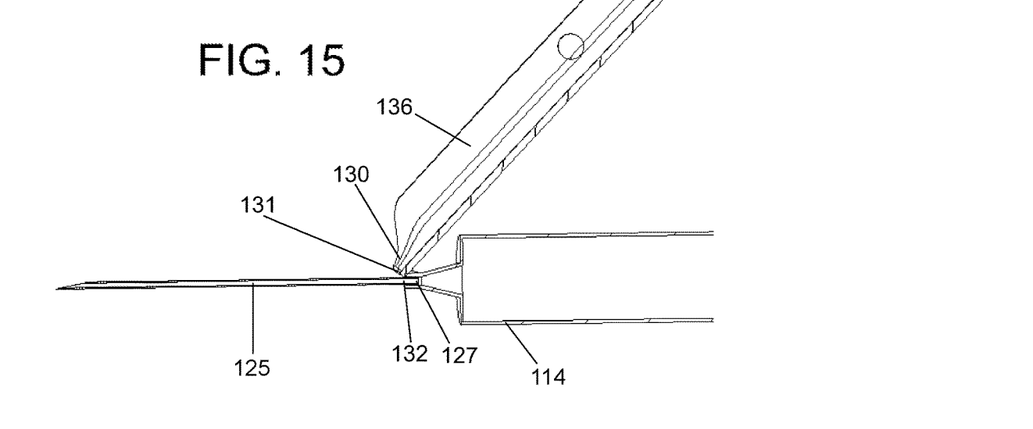
FIG. 15 is a side, cross-sectional view of a syringe with sheath in a retracted posture.
Figures 16, 17:
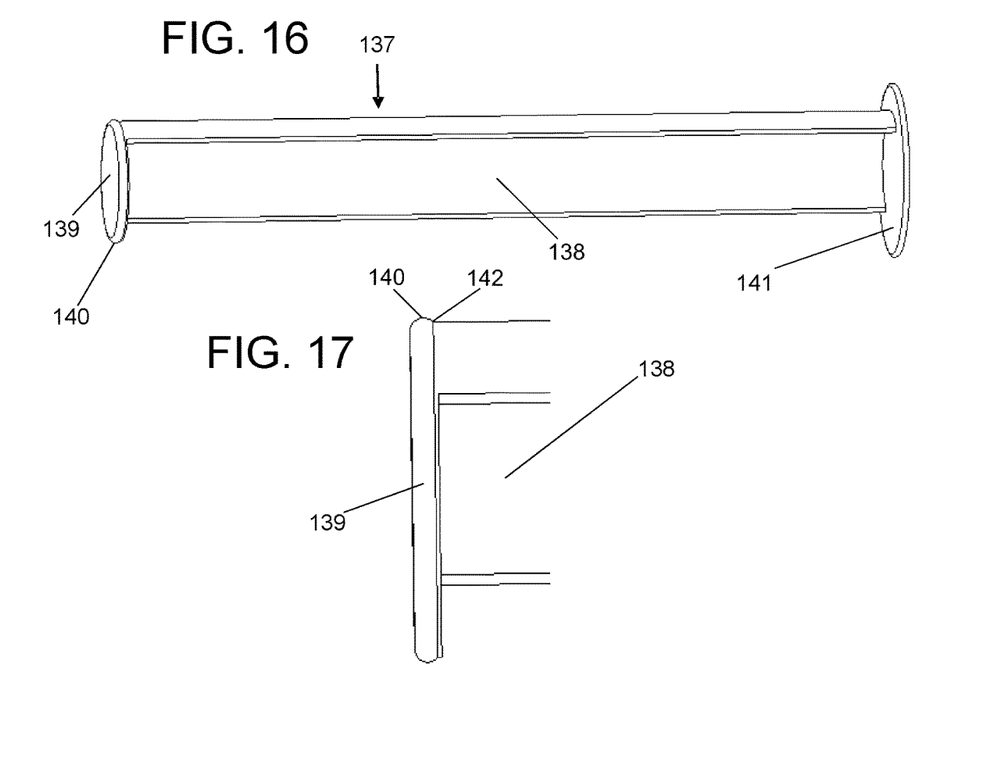
FIG. 16 is an axonometric view of a syringe plunger.
FIG. 17 is an enlarged, side detail view of a plunger sealing disc.

FIG. 8 is an axonometric view and FIG. 10 is a longitudinal cross-sectional, side view of another embodiment of a thermoformed syringe 110 with the body 111 having an integral, selectively rotating, cannula (needle) sheath 136. The syringe's tubular body 111 comprises barrel 114 with a flanged, proximal opening 118; a truncated, intermediary sealed, end wall 120 with a frustum passageway 124 distally accepting a cannula 125 with adhesive 129; and an integral, selectively rotating sheath 136 extending distally. At the open, proximal end 118 of barrel 114, a thermoformed, peripheral gripping flange 119 maintains the circular nature of the barrel 114 and assists the holding of the syringe 110 during filling and administering an injection. Thermoforming and sealing over a mandrel provide the tubular barrel 114 with a uniform diameter 112 and a smooth, truncated, end wall 120 with seal 121 creating a sealing flange 123. The stepped frustum, distal passageway 124 provides a visual, fluid communication between the fluid chamber 115 of the barrel 114 and a cannula 125. The cannula 125 has one end 126 sufficiently sharp to pierce the patient's skin and the other end 127 blunt to receive the affixing adhesive 129. FIGS. 11 and 12 show the remaining body length 136 distally beyond the frustum 124 is flattened, arcuately die-cut 156, and thermoformed slightly downward into a selectively rotating, trough sheath 136. FIGS. 13, 14, and 15 reveal its attachment sections are living hinges 130 providing selective posturing of the sheath 136 by a rotating interference between the proximal, central trough region 131 and the cannula base 132 due to arcuate cut 156. As the sheath 136 rotates, the interference causes a lengthening and distortion of the living hinges 130. Once over center, the living hinge geometries return, overpowering the hinge return memories. Along the sheath's sidewall 133 length, two detents 134 and 135 are formed in the sidewalls with a sufficient depth to engage the cannula 125 when the trough is formed providing selective sheath 136 rotation. FIGS. 16 and 17 display a plunger 137 in this embodiment which is injection molded in a manner to avoid a parting line traversing the liquid-tight ring seal interface 140. The entire sealing ring 139 remains in the B-side of the mold with the integral shaft 138 and finger pad 141 until tumbling out upon ejecting. The mold's parting line 142 occurs on the part profile above the interface 140 unaffecting its sealing engagement. The ring seal 139 becomes slightly compressed to overcome the resistance of the undercut in the mold's seal detail preventing a parting line 142. FIGS. 9 and 10 show this embodiment also features a shipping and handling, outer sheath 145. The sheath's tubular body 146 comprises barrel 146 with a flanged, proximal opening 148 and a truncated, sealed end wall 150 with seal 151 creating sealing flange 155. At the open, proximal end 148 of barrel 147, a thermoformed, peripheral gripping flange 149 maintains the circular nature of the barrel 146 and assists the side, die-cut openings 154 for the placement of the sheath 145. The outer sheath circumference 149 is sufficient to pass over the elliptical, seal selvage 122.

Figures 18, 19:
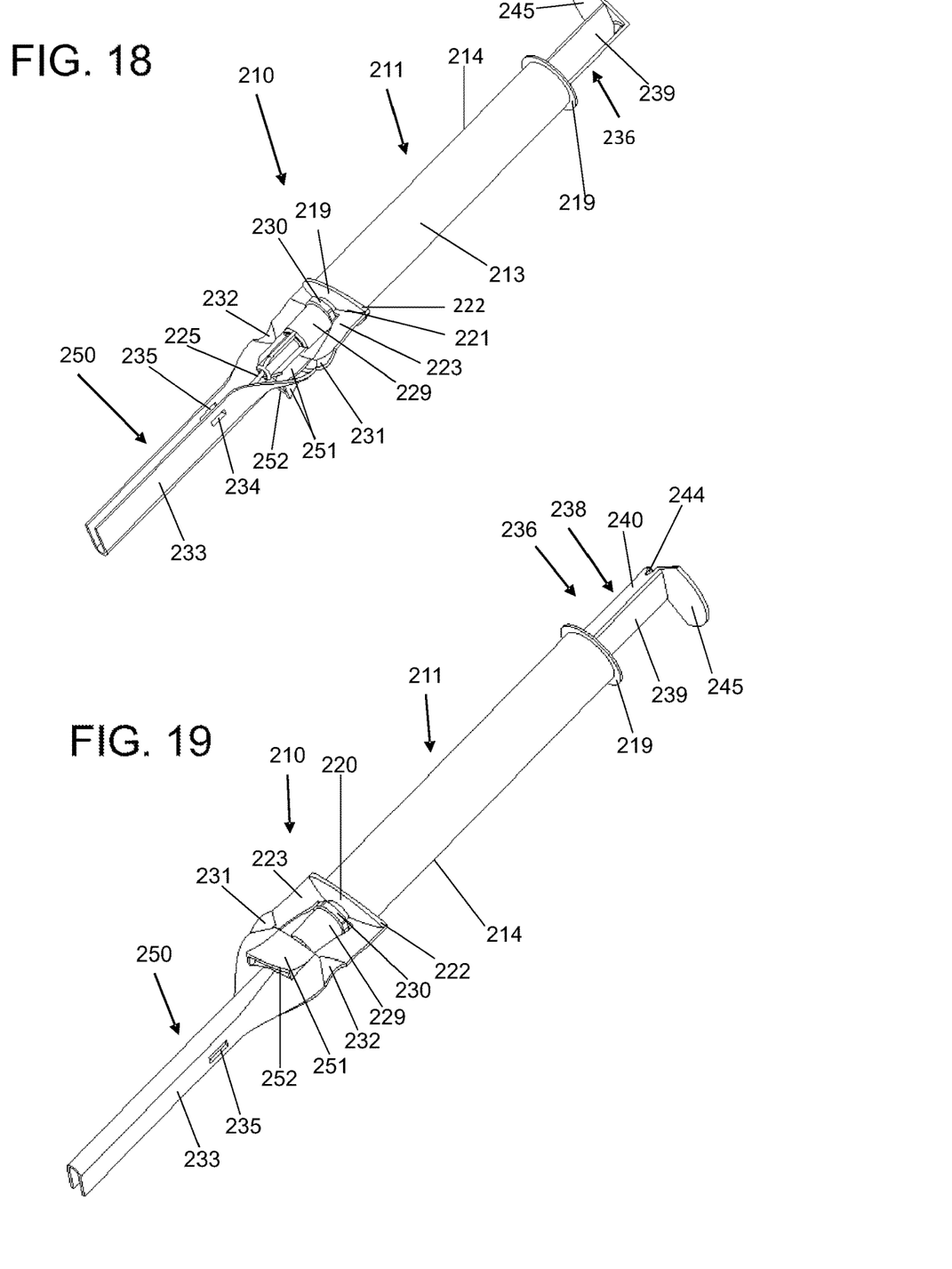
FIG. 18 is a bottom, axonometric view of a syringe with the luer-hubbed needle in place in accordance with an alternative embodiment of the invention.
FIG. 19 is a top, axonometric view of the thermoformed syringe of FIG. 18.
Figure 20:
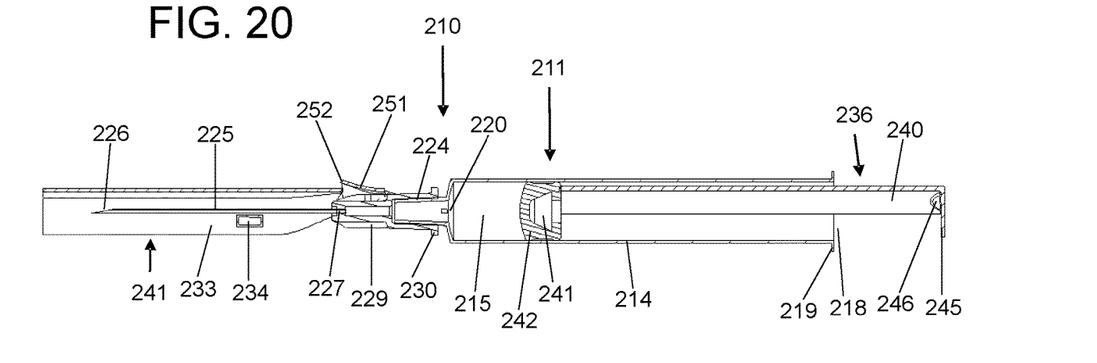
FIG. 20 is a longitudinal cross-sectional, side view of the thermoformed syringe of FIG. 18.
Figure 21:
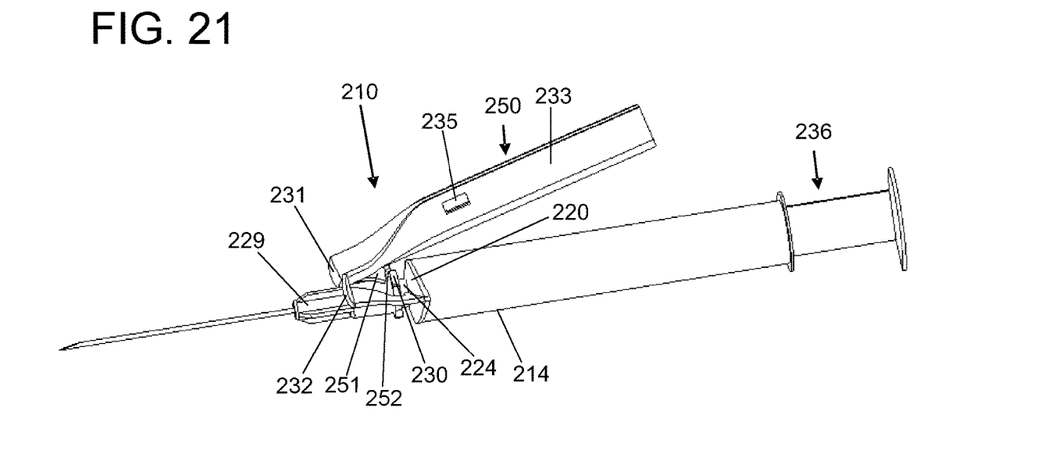
FIG. 21 is an axonometric view of a thermoformed syringe with a retracted sheath.
Figure 22:
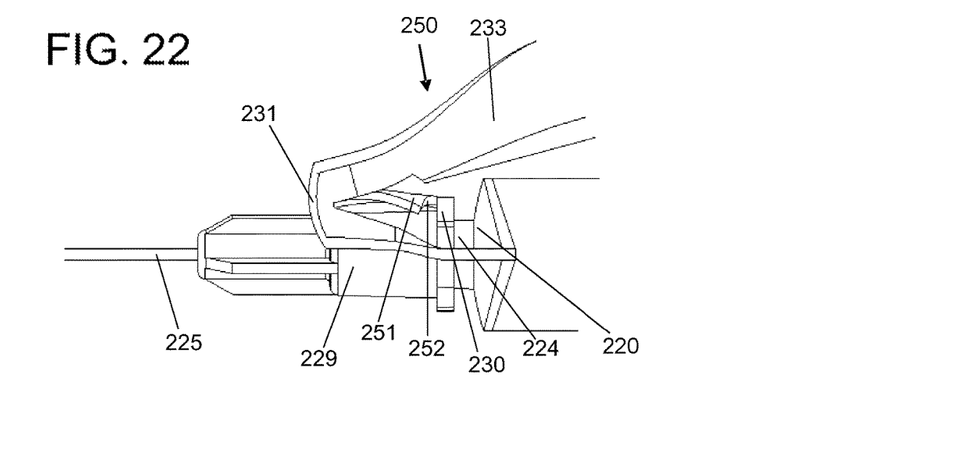
FIG. 22 is a side view of the thermoformed syringe.
Figure 23:
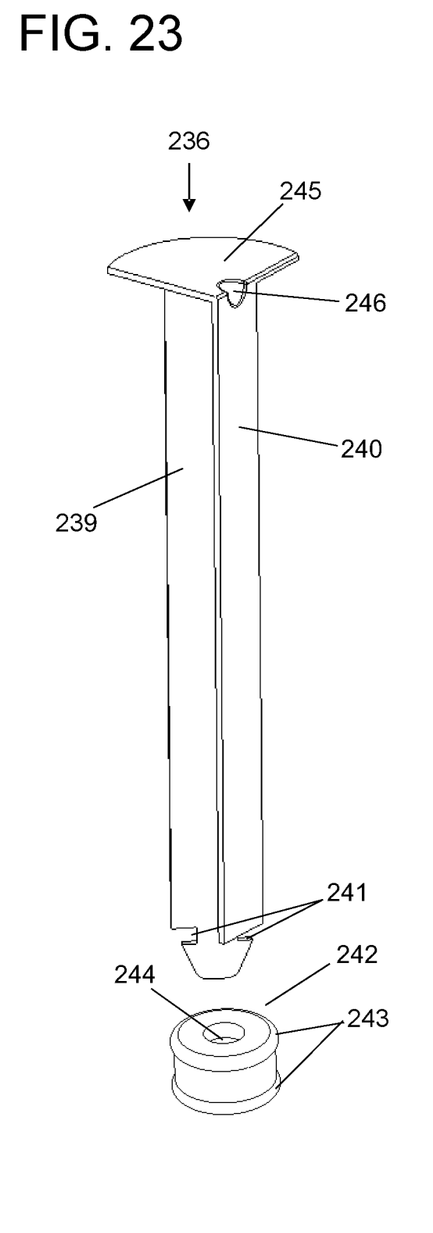
FIG. 23 is an axonometric view of a syringe's plunger with grommet.
Figure 24:
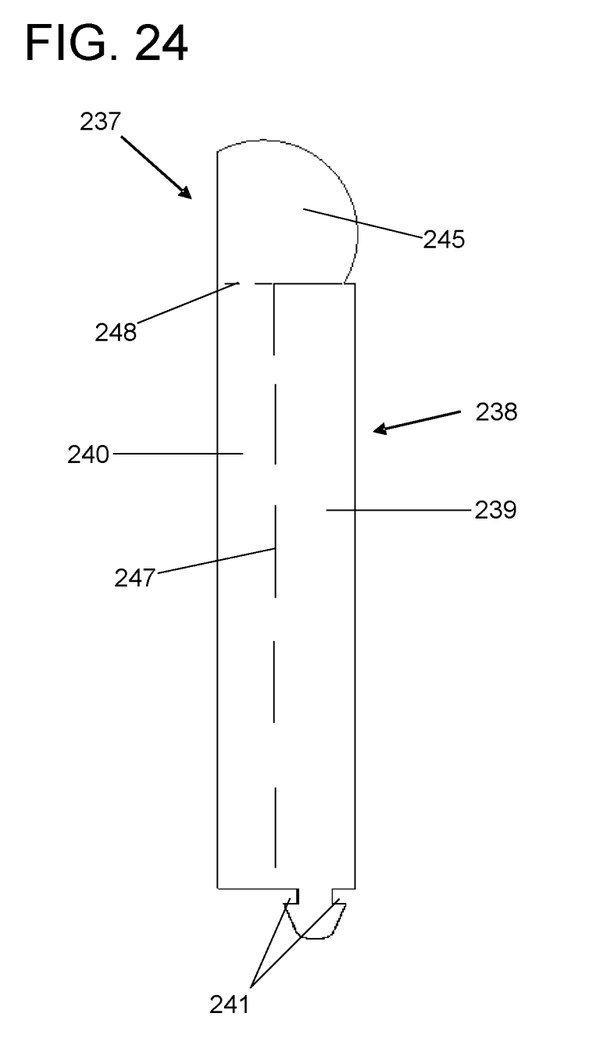
FIG. 24 is an axonometric view of the plunger's die-cut blank.

FIGS. 18, 19, and 20 disclose another embodiment of a thermoformed syringe 210 with the body 211 having an integral, selectively rotating, cannula (needle) sheath 250. The syringe's tubular body 211 comprises barrel 214 with a flanged, proximal opening 218; a paraboloidal, intermediary sealed, end wall 220 with a frustum passageway 224 distally accepting a luer hub 229 supporting cannula 225 with adhesive about its base 227; and an integral, selectively rotating sheath 250 extending distally. The end wall 220 may be either a symmetrical or an elliptical paraboloid. End wall 220's seal 221 produces a seal selvage 222 and seal flange 223. The frustum 224 is of sufficient length to provide visual, fluid communication between the fluid chamber 213 of the barrel 214 and a luer-hubbed cannula 225. FIGS. 18, 21 and 22 reveal the trough sheath's 250 attachment sections are biased living hinges 231 and 232 providing selective posturing of the sheath 250. This sheath 250 provides cannular 225 protection for its tip 226 with enclosing trough 233 with opposing, locking detents 234 and 235 for safe disposal. The opened sheath 250 provides a securing, single thread flight 252 on its surface 251 contacting a locking tab 230 of a luer hub 229. At the open, proximal end 218 of barrel 214, a thermoformed, peripheral gripping flange 219 maintains the circular nature of the barrel 214 and assists the holding of the syringe 210 during filling and administering an injection. FIGS. 23 and 24 also reveal the plunger 236 of this embodiment is die-cut from flat stock 237 and consists of a thermoformed V-shaped shaft 238 with members 239 and 240. Member 239 has distal cutouts 241 for engaging an internal recessed ring 244 within an elastomeric, sealing grommet 242 and a finger pad 245 thermally folded atop the shaft member 240 with a locking indent 246. The fold lines are 247 to create the V-shaped shaft 238 and 248 to form the finger pad 245. A pair of integral O-rings 243 of grommet 242 provide a fluid tight seal with syringe barrel side wall 214. The sealing grommet 242 must have the reverse geometry of the barrel's distal, end wall 220 for full content evacuation.

What is claimed is:
1. A syringe comprising:
 a tube having an open proximal end and a truncated, thermally sealed distal end comprising, a distally extending seal selvage flange comprising a fluid passageway fluidly communicating with an axially aligned cannula; and
 a shaft supporting a distal, fluid sealing disc and a finger pad at an opposite end moveably disposed within the tube.
2. The syringe as defined in claim 1 and further comprising:
 a flange on the open, proximal end.
3. The syringe as defined in claim 1 and further comprising:
 a tubular needle sheath having an operably sealed, distal end and attachment openings adjacent an open, proximal end.
4. A syringe comprising:
 a tube having an open proximal end comprising a fluid, frustum passageway partially extending within a distally extending seal selvage flange from an intermediary sealed, truncated distal end wall to a transverse, arcuate cut through the distally extending, seal selvage flange; and
 an integral, distal, trough sheath thermally formed within a remaining sealed flange, rotated about thermally impressed, biased living hinges to provide selective access to a distal, intravenous cannula or shielding with opposing rotations; wherein the distal, intravenous cannula is configured to provide interference with the integral, distal, trough sheath due to the transverse, arcuate cut;
 an arcuate shaft supporting a distal, fluid sealing disc and a finger pad at an opposite end, moveably disposed within the tube.
5. The syringe as defined in claim 4 and further comprising:
 a flange on the open, proximal end.

* * * * *